(12) United States Patent
Yatagai et al.

(10) Patent No.: US 9,612,193 B2
(45) Date of Patent: Apr. 4, 2017

(54) ELLIPSOMETRY SYSTEM

(75) Inventors: Toyohiko Yatagai, Nagareyama (JP);
Cense J. Abraham, Utsunomiya (JP)

(73) Assignee: UTSUNOMIYA UNIVERSITY,
Utsunomiya-shi, Tochigi (JP)

( * ) Notice: Subject to any disclaimer, the term of this patent is extended or adjusted under 35 U.S.C. 154(b) by 206 days.

(21) Appl. No.: 14/130,694

(22) PCT Filed: Jul. 9, 2012

(86) PCT No.: PCT/JP2012/067488
§ 371 (c)(1),
(2), (4) Date: Feb. 14, 2014

(87) PCT Pub. No.: WO2013/008784
PCT Pub. Date: Jan. 17, 2013

(65) Prior Publication Data
US 2014/0192364 A1    Jul. 10, 2014

(30) Foreign Application Priority Data
Jul. 12, 2011  (JP) .................................. 2011-154241

(51) Int. Cl.
*G01N 21/21* (2006.01)
*A61B 3/10* (2006.01)
(Continued)

(52) U.S. Cl.
CPC ............ *G01N 21/211* (2013.01); *A61B 3/102*
(2013.01); *G01B 9/02044* (2013.01);
(Continued)

(58) Field of Classification Search
CPC ............ G01N 21/211; G01N 21/4795; G01N 2021/1787; G01N 2021/213; G01N 21/17;
(Continued)

(56) References Cited

U.S. PATENT DOCUMENTS 1,007,346 A * 10/1911 Fery .......................... G01J 3/02
356/300
6,052,188 A *  4/2000 Fluckiger ............. G01N 21/211
356/369
(Continued)

FOREIGN PATENT DOCUMENTS

EP           1 095 259        5/2001
JP        2003-149049 A       5/2003
(Continued)

OTHER PUBLICATIONS

Machine Translation of JP Document JP 2007-298461 to Yoshiaki et al., from espacenet.*
(Continued)

*Primary Examiner* — Tarifur Chowdhury
*Assistant Examiner* — Mohamed K Amara
(74) *Attorney, Agent, or Firm* — Drinker Biddle & Reath LLP

(57) ABSTRACT

An ellipsometry system and a detection unit thereof are capable of achieving miniaturization and price reduction associated therewith. The ellipsometry system includes the detection unit that: has an optical polarization element; separates an interference polarization beam obtained by causing the object-reflected polarization beam and reference reflected polarization beam to interfere with each other into a plurality of interference polarization beams on a wavelength basis; and detects the respective separated polarization components in each wavelength. The optical polarization element: has a birefringence characteristic including a first refractive index and a second refractive index; receives the separated interference polarization beams of the respective wavelengths in a wavelength order and in a parallel manner; separates the separated interference polarization beam of each wavelength, on a polarization component basis, while transmitting the same, and outputs the respec-
(Continued)

tive separated polarization components in each wavelength in the same direction but along different optical axes.

6 Claims, 7 Drawing Sheets

(51) Int. Cl.
  *G01B 9/02* (2006.01)
  *G01N 21/47* (2006.01)
  *G02B 5/30* (2006.01)
  *G01J 4/00* (2006.01)
  *G02B 5/04* (2006.01)

(52) U.S. Cl.
  CPC .......... *G01B 9/02091* (2013.01); *G01J 4/00* (2013.01); *G01N 21/4795* (2013.01); *G02B 5/04* (2013.01); *G02B 5/3083* (2013.01); *G01B 2290/45* (2013.01); *G01B 2290/70* (2013.01)

(58) Field of Classification Search
  CPC ...... G01N 21/21; A61B 3/102; A61B 5/0066; A61B 5/0073; A61B 10/00; A61B 3/12; G01B 9/02044; G01B 9/02091; G01B 2290/45; G01B 2290/70; G01B 11/0675; G01B 9/02079; G01B 11/24; G01J 4/00; G01J 3/45; G01J 4/04; G02B 5/04; G02B 5/3083; G02B 5/3016; G02B 5/3025; G02B 27/286; G02B 5/30; G02B 27/28; G02B 27/10
  USPC .................................. 356/490–495
  See application file for complete search history.

(56) References Cited

U.S. PATENT DOCUMENTS

| | | | | |
|---|---|---|---|---|
| 7,061,613 | B1* | 6/2006 | Huang | G01J 4/04 |
| | | | | 356/364 |
| 2002/0126385 | A1* | 9/2002 | Asami | G01J 3/02 |
| | | | | 359/571 |
| 2002/0186373 | A1 | 12/2002 | Thoma et al. | |
| 2003/0016425 | A1 | 1/2003 | Tan et al. | |
| 2005/0259907 | A1* | 11/2005 | Tan | H04B 10/61 |
| | | | | 385/11 |
| 2007/0038040 | A1 | 2/2007 | Cense et al. | |
| 2008/0049323 | A1* | 2/2008 | Sugiyama | B29D 11/0074 |
| | | | | 359/489.02 |
| 2008/0309873 | A1* | 12/2008 | Levecq | A61F 9/008 |
| | | | | 351/209 |
| 2009/0149742 | A1* | 6/2009 | Kato | A61B 5/117 |
| | | | | 600/425 |
| 2012/0147326 | A1* | 6/2012 | Yatagai | A61B 3/1225 |
| | | | | 351/206 |
| 2013/0107272 | A1* | 5/2013 | Hirose | A61B 3/102 |
| | | | | 356/477 |
| 2013/0113925 | A1* | 5/2013 | Kim | G01B 9/02007 |
| | | | | 348/135 |
| 2013/0335740 | A1* | 12/2013 | Ishimaru | G01N 21/23 |
| | | | | 356/365 |
| 2015/0369586 | A1* | 12/2015 | Fukuhara | G01B 9/02058 |
| | | | | 356/479 |

FOREIGN PATENT DOCUMENTS

| | | |
|---|---|---|
| JP | 2007-298461 A | 11/2007 |
| JP | 2008-157710 A | 7/2008 |
| JP | 2008-538612 A | 10/2008 |
| WO | WO 2011/016437 | 2/2011 |

OTHER PUBLICATIONS http://olympusmicro.com/primer/java/prismsandbeamsplitters/polarizing/index.html.*
http://www.lajpe.org/june11/19_LAJPE_522_Adam_Usman_Preprint_corr_f.pdf.*
https://en.wikipedia.org/wiki/Nomarski_prism.*
https://en.wikipedia.org/wiki/Birefringence.*
http://photonics.intec.ugent.be/education/IVPV/res_handbook/v2ch03.pdf.*
Kouichi Muro et al., "Poly-Si/SiO$_2$ Laminated Walk-Off Polarizer Having a Beam-Splitting Angle of More Than 20°," Journal of Lightwave Technology, vol. 16, No. 1, Jan. 1998, pp. 127-133.
Kazuo Shiraishi et al., "Fabrication of spatial walk-off polarizing film exhibiting a large split angle by oblique silicon deposition," Optics Letters, vol. 23, No. 15, Aug. 1, 1998, pp. 1232-1234.

* cited by examiner

ELLIPSOMETRY SYSTEM

FIELD OF THE INVENTION

The present invention relates to an ellipsometry system for analyzing an object to be measured using polarization and a detection unit used in such ellipsometry system.

BACKGROUND ART

In recent years, research on optical tomographic imaging systems (hereinafter referred to as "OCT: Optical Coherence Tomographs") which visualize the depth structure of the inside of a biological body by making use of an interference effect of light has been advancing.

In particular, recently, from the fact that optical tomographic imaging systems are non-invasive to living bodies and have high resolving power, the optical tomographic imaging systems is not only used for tomographic imaging of eye retinas, but also be attempted to use for tomographic imaging of biological organs other than retinas, or other structures.

Under such circumstances, a polarization OCT system, which employs the optical tomographic imaging system combined with polarization detection, is known.

For example, such polarization OCT system delivers a light beam polarized at 45 degrees into a sample (an object to be measured) such as a biological organ, and combines a polarization beam reflected from the sample (hereinafter referred to as an "object-reflected polarization beam") with reference light. The polarization OCT system is capable of imaging an internal structure of the sample by separating the combined light beam into each polarization component, i.e. vertical polarization and horizontal polarization, and by analyzing such components (see, for example, Patent Documents 1, 2 and 3).

PRIOR ART REFERENCES

Patent Documents

Patent Document 1: Japanese Laid-Open Patent Application No. 2008-157710
Patent Document 2: US Patent Application Publication No. 2007/0038040A1
Patent Document 3: Japanese National Phase Publication No. 2008-538612

SUMMARY OF THE INVENTION

Problems to be Solved by the Invention

However, the polarization OCT systems described in each patent document above require the use of a polarization beam splitter for separating the object-reflected polarization beam and reference light and an optical line sensor for detecting each polarization component. In particular, in such polarization OCT systems, it is necessary to arrange two optical line sensors in such a manner that their respective optical axes are at right angles to each other for a structural reason of the polarization beam splitter. Thus, it is difficult to achieve miniaturization and price reduction associated therewith.

The present invention is devised to solve the above problems. An object of the present invention is to provide an ellipsometry system, and the like, that uses polarization, which is capable of achieving miniaturization and price reduction associated therewith.

Problem Solving Means (1) An ellipsometry system of the present invention for solving the above-described problems, analyzes an object to be measured using polarization. The ellipsometry system includes: a polarization beam generation unit that has a light source, and generates a polarization beam based on an outgoing light beam emitted from the light source; a polarization beam splitter that splits the generated polarization beam into a first polarization beam and a second polarization beam; a reference polarization beam unit that generates, from the first polarization beam, a reference polarization beam to be used as reference light when generating a tomographic image; a measurement unit that irradiates the object to be measured with the second polarization beam, and outputs an object-reflected polarization beam reflected from the object to be measured based on such irradiation; a detection unit that receives an interference polarization beam obtained by causing the reference polarization beam and the object-reflected polarization beam to interfere with each other and detects the interference polarization beam on a different polarization component basis; and a generation unit that generates the tomographic image of the object to be measured based on the polarization beam detected on a polarization component basis, wherein the detection unit has: a diffraction grating that separates the received interference polarization beam on a wavelength basis; a polarization optical element that: has a birefringence characteristic including a first refractive index and a second refractive index; receives the separated interference polarization beams of the respective wavelengths in a wavelength order and in a parallel manner; separates the separated interference polarization beam of each wavelength on a polarization component basis, while transmitting the same, and outputs the respective separated polarization components in each wavelength in the same direction but along different optical axes; and detection section that has two sensor arrays detecting the interference polarization beams of each wavelength separated on a polarization component basis, respectively, the two sensor arrays being arranged side by side with a predetermined distance interval therebetween, and wherein a thickness in a transmission direction in the polarization optical element through which the interference polarization beams transmit is different for each wavelength of the interference polarization beam.

By employing such configuration, the ellipsometry system of the present invention is capable of separating, in the polarization optical element, the interference polarization beams of each wavelength to be used when generating a tomographic image on a polarization component basis and outputting the respective polarization components in such a manner that their optical axes are arranged in the same direction. Therefore, the ellipsometry system of the present invention is also capable of detecting the interference polarization beams of each wavelength on a polarization component basis by the detection section having two sensor arrays arranged side by side with a predetermined distance interval therebetween.

Accordingly, the ellipsometry system of the present invention allows for a reduction in the number of components, such as a retaining member for retaining the detection section, as compared to the case in which a polarization optical element is a polarization beam splitter that requires two line sensors to be separately arranged at different locations and that also requires outputting of the respective polarization components along optical axes which are at right angles to each line sensor. Therefore, it is possible to achieve miniaturization thereof and price reduction associated with such miniaturization.

(2) The ellipsometry system of the present invention is configured so that the thickness of the polarization optical element in the transmission direction gradually increases from a side on which an interference polarization beam having a short wavelength is incident to a side on which an interference polarization beam having a long wavelength is incident.

By employing such configuration, the ellipsometry system of the present invention is capable of easily and precisely adjusting, in the polarization optical element, the separation intervals when separating the polarization components on a wavelength basis. Therefore, each polarization component can be detected in an accurate manner.

(3) The ellipsometry system of the present invention may be configured so that an entrance face of the polarization optical element for the interference polarization beams has a curved surface.

By employing such configuration, the ellipsometry system of the present invention is capable of precisely adjusting the separation intervals when separating the polarization components on a wavelength basis.

(4) The ellipsometry system of the present invention may be configured so that an entrance face of the polarization optical element for the interference polarization beams has a flat surface.

By employing such configuration, the ellipsometry system of the present invention is capable of easily manufacturing a polarization optical element, and thus, price reduction can be achieved.

(5) The ellipsometry system of the present invention may be configured so that the relationship among the distance interval "d" of the two sensor arrays in the detection section, the first refractive index "$n_1$", the second refractive index "$n_2$", an angle "$\theta$" between an optical axis of an incident light beam (separated interference polarization beams) and an axis of the first refractive index, and the thickness L in the transmission direction at at least one of a minimum wavelength and maximum wavelength, satisfies Formula A.

$$L = \frac{d}{\frac{[(n_1)^2 - (n_2)^2] \cdot \tan\theta}{(n_1)^2 + (n_2)^2 \cdot (\tan\theta)^2}}$$ [Formula 1]

By employing such configuration, the ellipsometry system of the present invention is capable of forming a polarization optical element by defining two refractive indices of fast and slow axes, etc. in a birefringence material and an angle of inclination with respect to an incident light beam of the fast axis. Therefore, it is possible to form a polarization optical element without specifying the material, etc., and when the shape of such polarization optical element is altered, it is also possible to use various sensor arrays.

(6) A detection unit of the present invention to be used in an ellipsometry system for analyzing an object to be measured using polarization detects, on a different polarization component basis, interference polarization beam which is obtained by causing a reference polarization beam, which is used as reference light when generating a tomographic image and which is generated based on a predetermined polarization beam, and an object-reflected polarization beam, which is reflected from the object to be measured based on an irradiation of the object to be measured with a part of the predetermined polarization beam, to interfere with each other. The detection unit includes: a diffraction grating that separates the received interference polarization beam into a plurality of interference polarization beams on a wavelength basis; a polarization optical element that: has a birefringence characteristic including a first refractive index and a second refractive index; receives the separated interference polarization beams of the respective wavelengths in a wavelength order and in a parallel manner; separates the separated interference polarization beam of each wavelength into a plurality of separated interference polarization on a polarization component basis, while transmitting the same, and outputs the respective separated polarization components in each wavelength in the same direction but along different optical axes; and detection section that has two sensor arrays detecting the interference polarization beams of each wavelength separated on a polarization component basis, respectively, the two sensor arrays being arranged side by side with a predetermined distance interval therebetween, and wherein a thickness in a transmission direction in the polarization optical element through which the interference polarization beams transmit is different for each wavelength of the interference polarization beam.

By employing such configuration, the detection unit of the present invention is capable of separating, in the polarization optical element, the interference polarization beams of each wavelength to be used when generating a tomographic image on a polarization component basis and outputting the respective polarization components in such a manner that their optical axes are arranged in the same direction. Therefore, the detection unit of the present invention is also capable of detecting the interference polarization beams of each wavelength on a polarization component basis by the detection section having two sensor arrays arranged side by side with a predetermined distance interval therebetween.

Accordingly, the detection unit of the present invention allows for a reduction in the number of components, as compared to the case in which a polarization beam splitter that causes each of the polarization components to exit along optical axes which are at right angles to each other and that requires two line sensors to be separately arranged at different locations, is used as a polarization optical element, and thus, miniaturization thereof can be achieved.

Effect of the Invention

The ellipsometry system and the detection unit of the present invention allow for a reduction in the number of components, as compared to the case in which a polarization beam splitter that causes the respective polarization components to exit along optical axes which are at right angles to each other, and that requires two line sensors to be separately arranged at different locations, is used as a polarization optical element. Therefore, it is possible to achieve miniaturization of the system itself or the detection unit itself, and price reduction associated with such miniaturization.

BRIEF DESCRIPTIONS OF THE DRAWINGS

EMBODIMENTS OF THE INVENTION

Hereinafter, embodiments of the present invention will be described with reference to the figures thereof.

It should be noted that, in the embodiments described below, the ellipsometry system and detection unit of the present invention are applied to an optical tomographic imaging system which generates a tomographic image of an eye fundus by use of polarization, and a detection unit used in such system.

[Summary of Optical Tomographic Imaging System]

Figure 1:
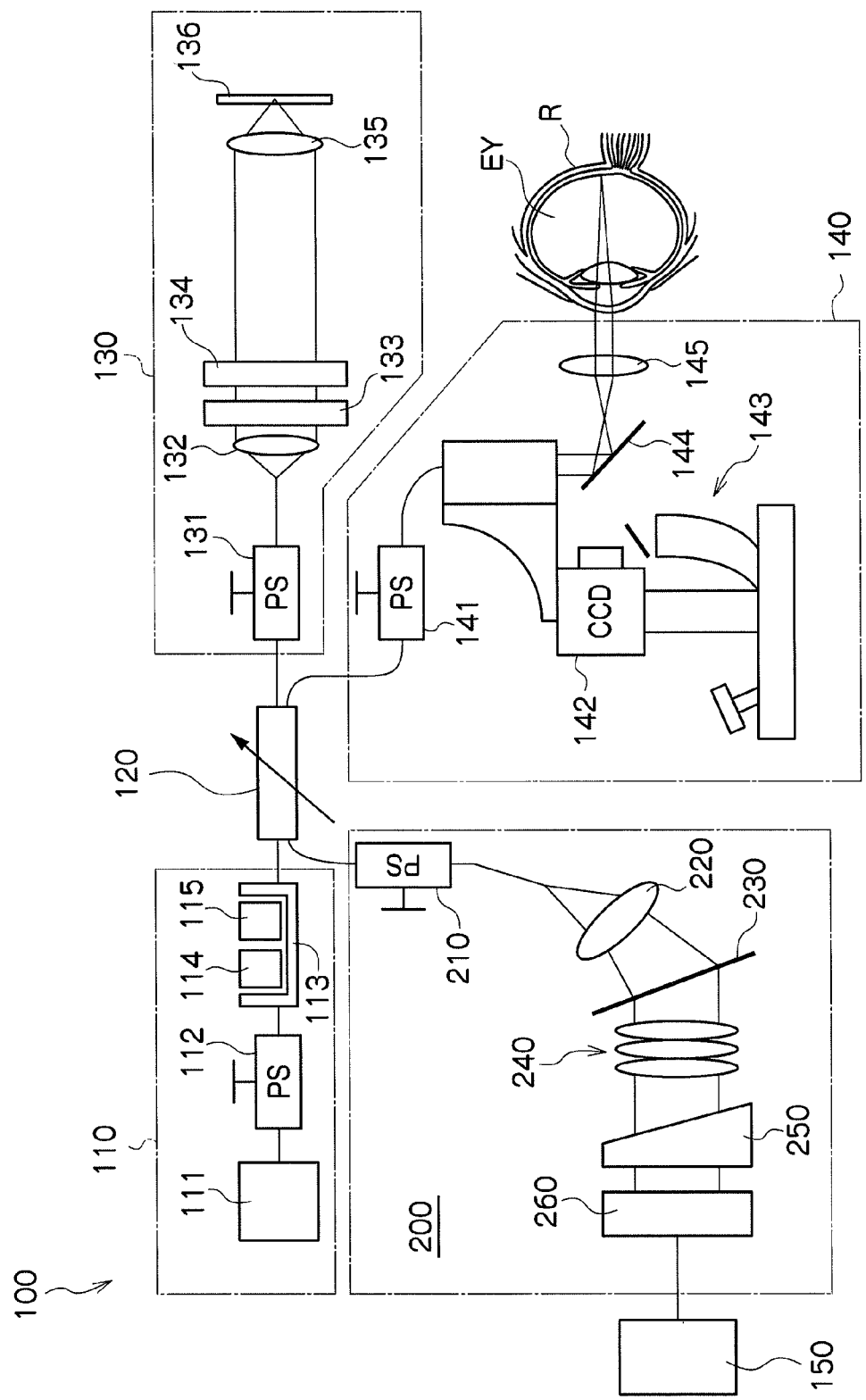
FIG. 1 is a block diagram illustrating the configuration, in an embodiment, of an optical tomographic imaging system that uses polarization according to the present invention.

First, a schematic configuration of optical tomographic imaging system 100 of the present embodiment will be described using FIG. 1. FIG. 1 is a block diagram illustrating the configuration of optical tomographic imaging system 100 of the present embodiment.

Optical tomographic imaging system 100 of the present embodiment is an OCT-measuring device which makes use of an adaptively-controlled optics system (AO) technique and obtains a tomographic image of an object, which is an inspection target (i.e. eyeball EY and, in particular, retina R, in the present embodiment), by use of polarization and an interference effect of such polarization.

Optical tomographic imaging system 100 polarizes a light source beam (i.e. an optical outgoing beam) emitted from light source 111 and splits the same into an object scanning light beam (hereinafter referred to as an "object scanning polarization beam") to be delivered into the inspection target and a reference light beam (hereinafter referred to as a "reference polarization beam"), which serves as a reference. In addition, optical tomographic imaging system 100 causes an object-reflected light beam (hereinafter referred to as an "object-reflected polarization beam"), which is the object scanning polarization beam delivered into the object and reflected thereat, and a reference reflected light beam (hereinafter referred to as a "reference reflected polarization beam"), which is the reference polarization beam reflected by a predetermined mirror, to interfere with each other.

Optical tomographic imaging system 100 separates, on a wavelength basis, an interference polarization beam obtained by causing the object-reflected polarization beam and reference reflected polarization beam to interfere with each other, and then, detects light intensities of various polarization components, including a horizontal polarization component and a vertical polarization component in each wavelength. Further, optical tomographic imaging system 100 generates a tomographic image of retina R including the depth direction of retina R, based on the detected light intensity of each of the polarization components.

In particular, as shown in FIG. 1, optical tomographic imaging system 100 has: polarization beam generation unit 110, which generates a predetermined polarization beam (hereinafter referred to as a "source polarization beam") from a light source beam emitted from light source 110; and optical splitter/coupler 120, which splits the source polarization beam into the reference polarization beam and the object scanning polarization beam and causes the reference reflected polarization beam and the object-reflected polarization beam to interfere with each other.

In addition, optical tomographic imaging system 100 has: reference light unit (hereinafter also referred to as "reference polarization beam unit") 130, which causes the reference reflected polarization beam to enter optical splitter/coupler 120 after allowing such reference polarization beam to reflect; and inspection unit (hereinafter also referred to as "measurement unit") 140, which causes the object-reflected polarization beam to enter optical splitter/coupler 120 after allowing the object to be irradiated with the object scanning polarization beam.

Moreover, optical tomographic imaging system 100: has detection unit 200, which separates, on a wavelength basis, an interference polarization beam obtained by causing the object-reflected light beam and reference reflected light beam to interfere with each other and detects polarization components in each wavelength; and image generation unit (hereinafter also referred to as a "generation unit") 150, which generates and outputs a tomographic image of the object based on the light intensity of each of the detected polarization components in each wavelength.

[Configuration of Optical Tomographic Imaging System]

Next, the configuration of optical tomographic imaging system 100 of the present embodiment will be described using FIGS. 1 and 2 above. FIGS. 2(A) and 2(B) are, respectively, a plan view and side view illustrating the configuration of part of detection unit 200 according to the present embodiment.

Polarization beam generation unit 110 generates the source polarization beam based on the light source beam, which is temporally and partially coherent light.

For example, polarization beam generation unit 110 of the present embodiment is composed of a super luminescent diode (SLD) or ultrashort pulsed laser, and has: light source 111 which emits a light source beam; in-line type polarization controller 112 which controls a polarization state; optical isolator 114 which is provided on fiber bench 113 and which performs a predetermined calibration; and polarization modulator 115 which is provided on fiber bench 113 and which modulates the emitted light source beam to a predetermined drive waveform (for example, a rectangular wave having a maximum frequency of 29,300 Hz) and generates a source polarization beam.

Optical splitter/coupler (i.e. polarization beam splitter) 120 splits, by an optical fiber or beam splitting prism, etc., the incident source polarization beam into an object scanning polarization beam and reference polarization beam which are, respectively, output to inspection unit 140 and reference light unit 130.

For example, optical splitter/coupler 120 of the present embodiment has a predetermined splitting ratio (e.g. a splitting ratio ranging approximately from 50:50 to 80:20), and splits the incident light source beam based on such splitting ratio and outputs the split beam to each of reference light unit 130 and inspection unit 140.

In addition, the object-reflected polarization beam, which is reflected from the object, of inspection unit 140 and the reference reflected polarization beam, which is reflected in reference light unit 130, enter optical splitter/coupler 120.

Then, optical splitter/coupler 120 causes the incident object-reflected polarization beam and reference reflected polarization beam to interfere with each other on a wavelength basis, and outputs the resultant interference polarization beam to detection unit 200.

For example, optical splitter/coupler 120 of the present embodiment has a predetermined coupling ratio (e.g. a coupling ratio ranging approximately from 50:50 to 80:20). Furthermore, optical splitter/coupler 120 causes the incident object-reflected polarization beam and reference reflected polarization beam to interfere with each other by coupling them based on such coupling ratio and outputs the resultant interference polarization beam to detection unit 200.

Reference light unit 130 is, essentially, a unit for generating a reference reflected light beam that serves as a reference by making use of an optical path having the same length as that of an optical path of the object scanning polarization beam (object-reflected polarization beam).

In particular, reference light unit 130 has: in-line type polarization controller 131 which controls a polarization state; transformation lens 132 which transforms the reference light beam into parallel light and the reference reflected light beam, which is parallel light, into a focused beam; variable natural density filter (ND filter) 133; analyzer 134; transformation lens 135 which transforms the reflected reference reflected light beam into parallel light and the reference light beam, which is parallel light, into a focused beam; and reflective mirror 136 which reflects the reference reflected light.

Inspection unit 140 scans eyeball EY (in particular, retina R) with the object scanning polarization beam and outputs the object-reflected polarization beam which is reflected from eyeball EY, after such scanning, to optical splitter/coupler 120.

In particular, inspection unit 140 has: in-line type polarization controller 141 which controls a polarization state; slit lamp device 143 which has CCD camera 142 and which scans eyeball EY based on the object scanning polarization beam; and various lenses 144, 145 for scanning the eyeball with an object scanning polarization beam.

While separating, on a wavelength basis, an interference light beam (hereinafter referred to as an "interference polarization beam") generated by coupling the object-reflected polarization beam and the reference reflected polarization beam, detection unit 200 also separates the interference polarization beam on a different polarization component basis, and thus detects light intensities of the light beam on a wavelength basis and on a polarization component basis.

In particular, as shown in FIGS. 1 and 2, detection unit 200 has: in-line type polarization controller 210 which controls a polarization status; first transformation lens 220 which transforms the incident interference polarization beam into predetermined light; diffraction grating 230 which separates the transformed interference polarization beam on a wavelength basis; and second transformation lens 240 for focusing each wavelength onto a corresponding position.

In addition, detection unit 200 has: polarization optical element 250 which separates the separated interference polarization beam of each wavelength, on a polarization component basis, and outputs the separated light in the same direction but along different optical axes; and detection device 260 provided with two sensor arrays 261, 262 which detect light intensities in the interference polarization beam of each wavelength separated on a polarization component basis.

The details of diffraction grating 230, polarization optical element 250, and the various parts in detection device 260 will be provided below.

Image generation unit 150 has an image display device such as a monitor, and generates a three-dimensional optical tomographic image of the retina of the eyeball (i.e. a three-dimensional retina tomographic image) based on a change in the light beam (i.e. a change in light intensities) for each wavelength and for each polarization component detected by detection unit 200 and causes the image display device to display the generated optical tomographic image thereon.

[Configuration of Detection Unit]

Next, the details of detection unit 200 of the present embodiment will be described using FIGS. 2 and 3 above. FIG. 3 is a diagram describing a line sensor in detection device 260 of the present embodiment.

First transformation lens 220 is formed by, for example, a collimator lens and, after transforming the interference polarization beam input into detection unit 200 into parallel light, outputs such parallel light to diffraction grating 230.

Diffraction grating 230 has slits, and separates the incident collimated interference polarization beam into a plurality of interference polarization beams, on a wavelength basis, by the diffraction resulting from slits. A slit surface formed with such slits is arranged with an inclination of a predetermined angle such that the first-order light of the plurality of interference polarization beams can enter second transformation lens 240. Namely, diffraction grating 230 of the present embodiment is arranged such that the slit surface is inclined to a predetermined angle based on an angle of the zero-order light of the incident interference polarization beam and angle at which the separated interference polarization beams exit.

Figures 2A, 2B:
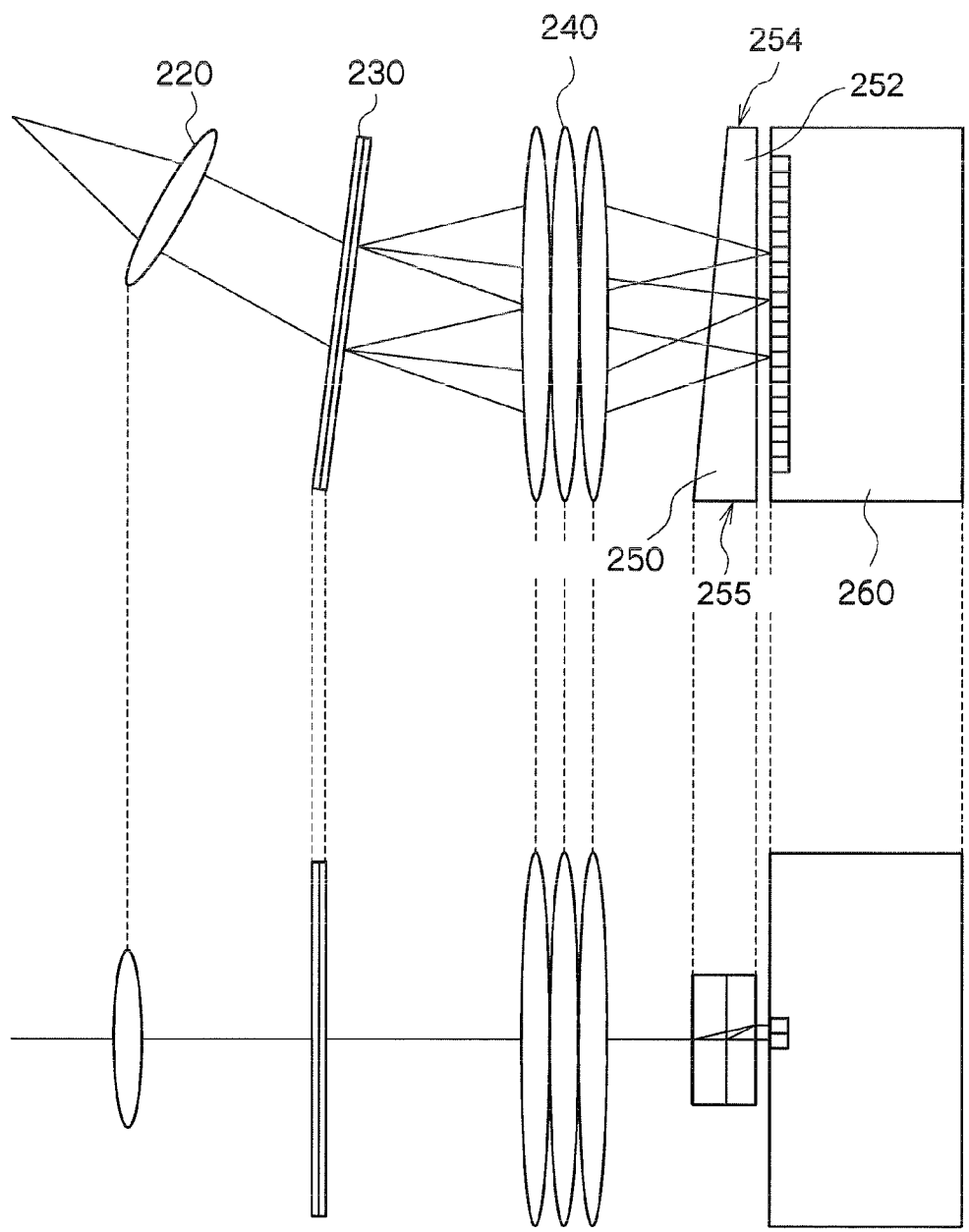
FIG. 2(A) is a plan view illustrating the configuration of part of a detection unit of an embodiment and FIG. 2(B) is a side view illustrating the configuration of part of a detection unit of an embodiment.
Figure 3:
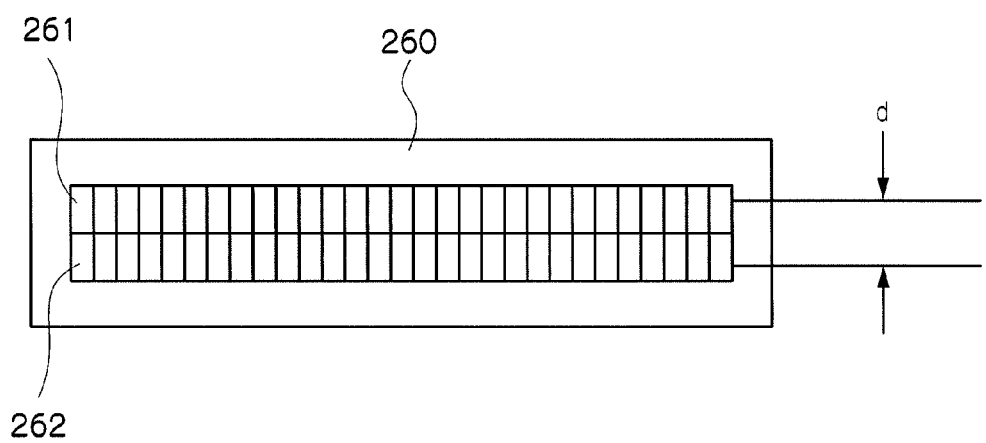
FIG. 3 is a diagram describing a line sensor in a detection device of an embodiment.

Second transformation lens 240 is formed such that the interference polarization beams, which are separated for each wavelength and are the first-order light output from diffraction grating 230, enters polarization optical element 250, along a light-incident surface of polarization optical element 250, from a first end thereof (e.g. an end in the upper portion in the plane of the paper in FIG. 2(A)) to a second end thereof (e.g. an end in the lower portion in the plane of the paper in FIG. 2(A)), which is different from the first end. Namely, second transformation lens 240 is a lens that causes the interference polarization beams separated on a wavelength basis to be arranged in order of length of wavelength from the first end to the second end of the light-incident surface of polarization optical element 250, and causes such beams to enter polarization optical element 250.

For example, in the present embodiment, second transformation lens 240 is composed of an aspheric lens. Second transformation lens 240 is configured such that, for a blue interference polarization beam having a short wavelength, second transformation lens 240 allows such beam to transmit through the first-end side of polarization optical element 250 to be focused on sensor arrays 261, 262, and, for a red interference polarization beam having a long wavelength, second transformation lens 240 allows such beam to transmit through the second-end side of polarization optical element 250 to be focused on sensor arrays 261, 262.

It should be noted that, as long as second transformation lens 240 can allow a blue interference polarization beam having a short wavelength to transmit through the first-end side of polarization optical element 250 to be focused on sensor arrays 261, 262 and can allow a red interference polarization beam having a long wavelength to transmit through the second-end side of polarization optical element 250 to be focused on sensor arrays 261, 262, it may be composed of various lenses such as a planar lens or spherical lens, in place of an aspheric lens.

Interference polarization beams separated on a wavelength basis enter polarization optical element 250 in a wavelength order and a parallel manner. Polarization optical element 250 has birefringence characteristics having a first refractive index and a second refractive index that fulfill predetermined conditions. In addition, such polarization optical element 250 separates the incident interference polarization beam of each wavelength, on a polarization component basis, while transmitting such interference polarization beam of each wavelength, and outputs the respective separated polarization components of the interference polarization beam in each wavelength in the same direction but along different optical axes.

The details of the configuration in polarization optical element 250 will be described below.

Detection device 260 has two sensor arrays 261, 262 each of which detects the interference polarization beams of each wavelength separated on a polarization component basis, respectively and is formed by arranging such two sensor arrays 261, 262 side by side with a predetermined distance interval therebetween.

In particular, as shown in FIG. 3, detection device 260 has two sensor arrays (hereinafter also referred to as "first line sensor and second line sensor") 261 and 262 which are arranged side by side in a spaced manner with a predetermined distance (hereinafter referred to as the "sensor interval") therebetween in the same plane and each of which detects the interference polarization beam of each wavelength on a polarization component basis, respectively.

First line sensor 261 and second line sensor 262 are line scan cameras having CCD elements, and output, in each wavelength, light intensity information of the interference polarization beam each of which is received at a corresponding CCD element, on a polarization component basis.

For example, detection device 260 of the present embodiment is formed by two line sensors arranged side by side with a space of 10 µm therebetween, based on the central axis.

[Configuration of Polarization Optical Element]

Next, the configuration in polarization optical element 250 of the present embodiment and the principles thereof will be described using FIGS. 4 to 7.

Figure 4:
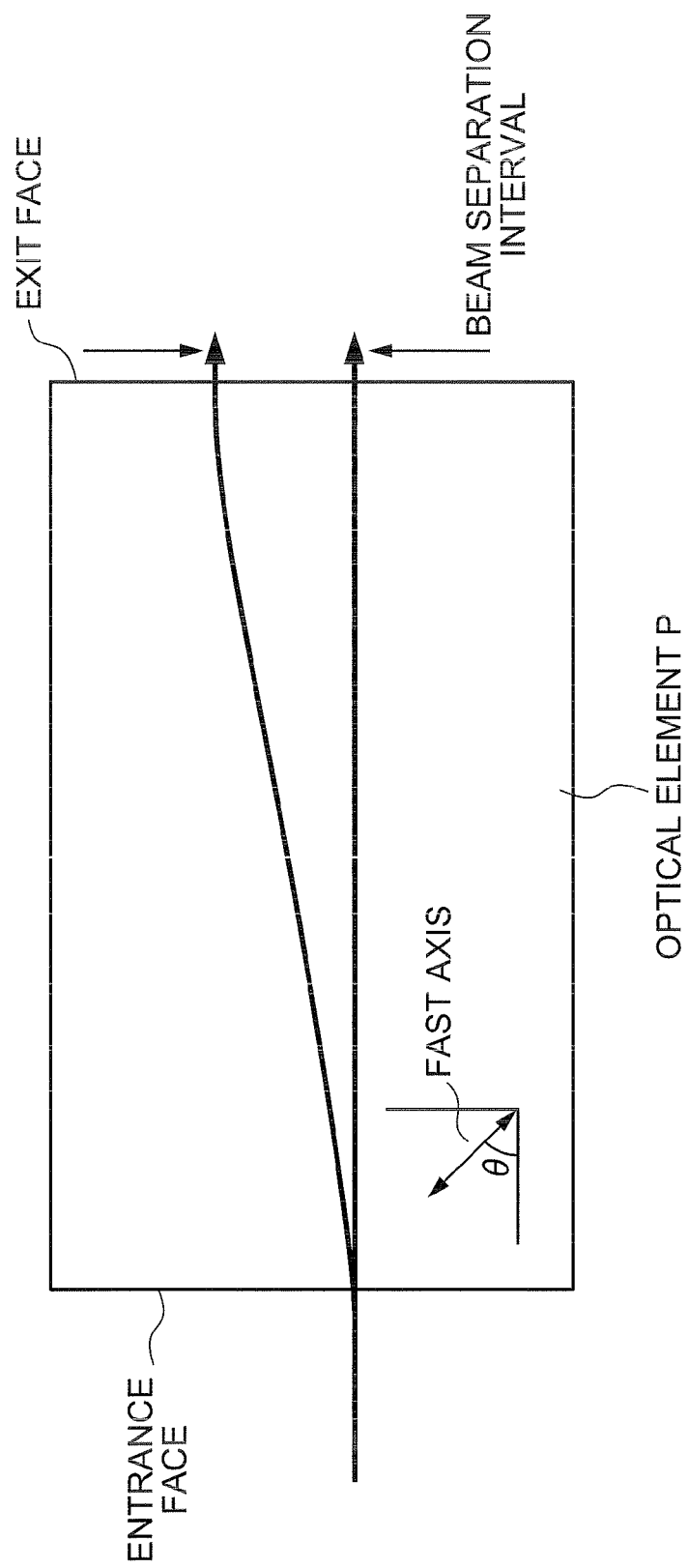
FIG. 4 is a diagram describing the separation of polarization components in a typical optical element formed with a fast axis inclined at θ=45 degrees.
Figure 5:
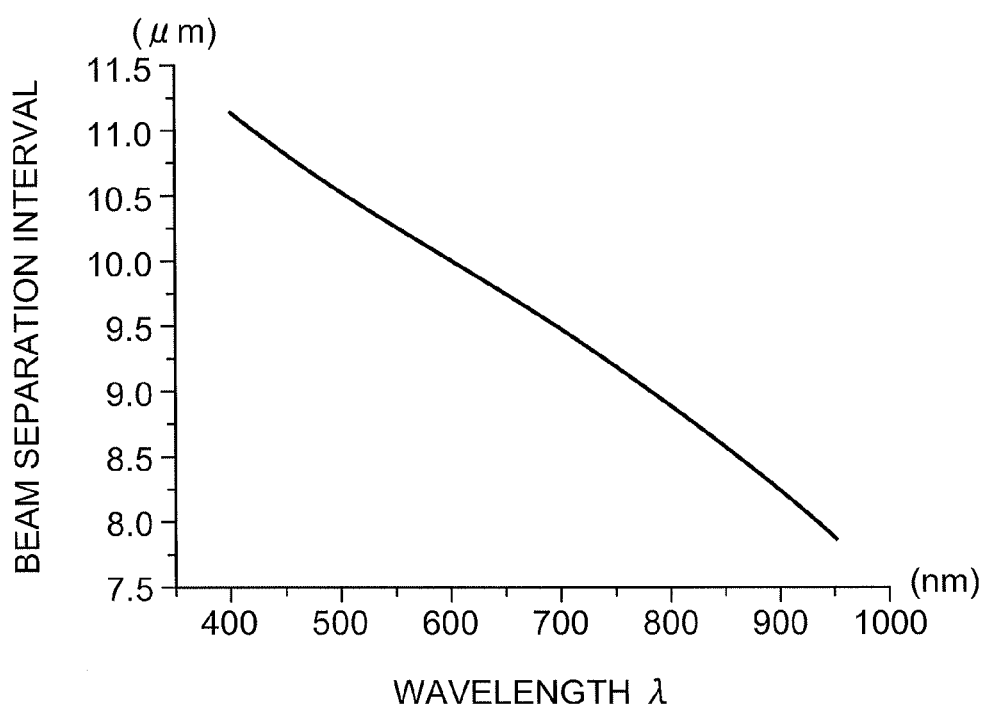
FIG. 5 is a graph illustrating the relationship between a beam separation interval and a wavelength.
Figure 6:
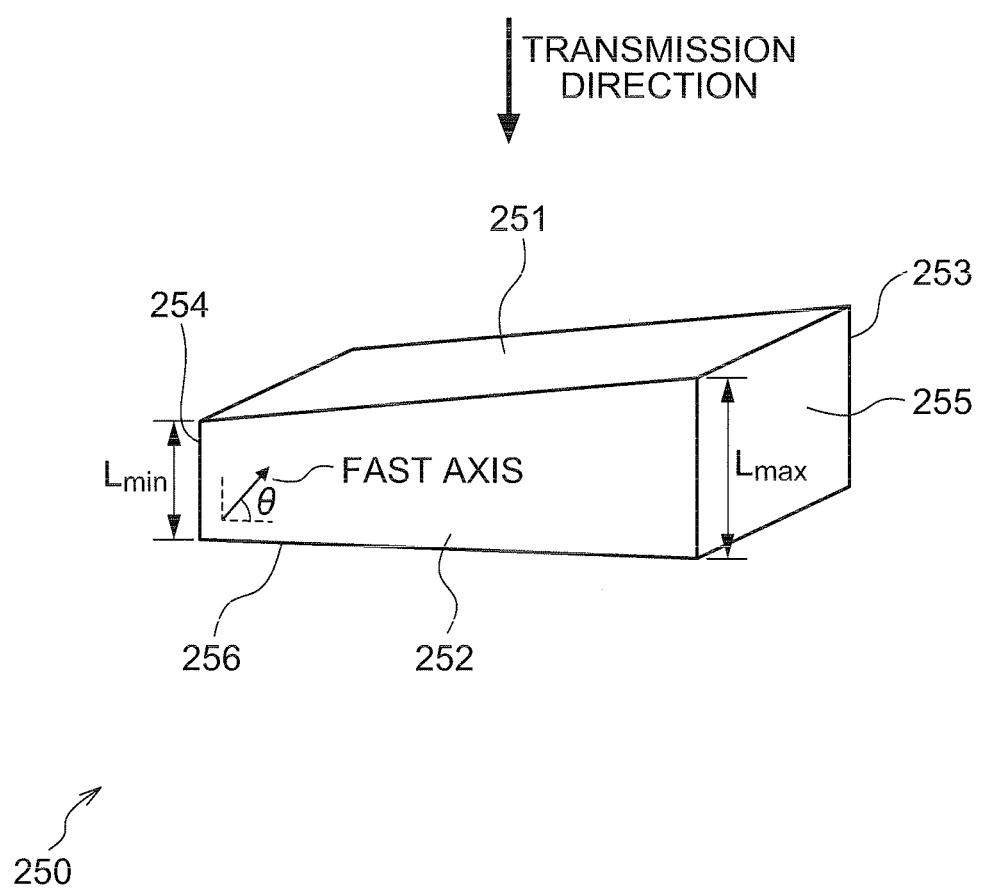
FIG. 6 is a configuration diagram illustrating the configuration of a polarization optical element of an embodiment.
Figure 7:
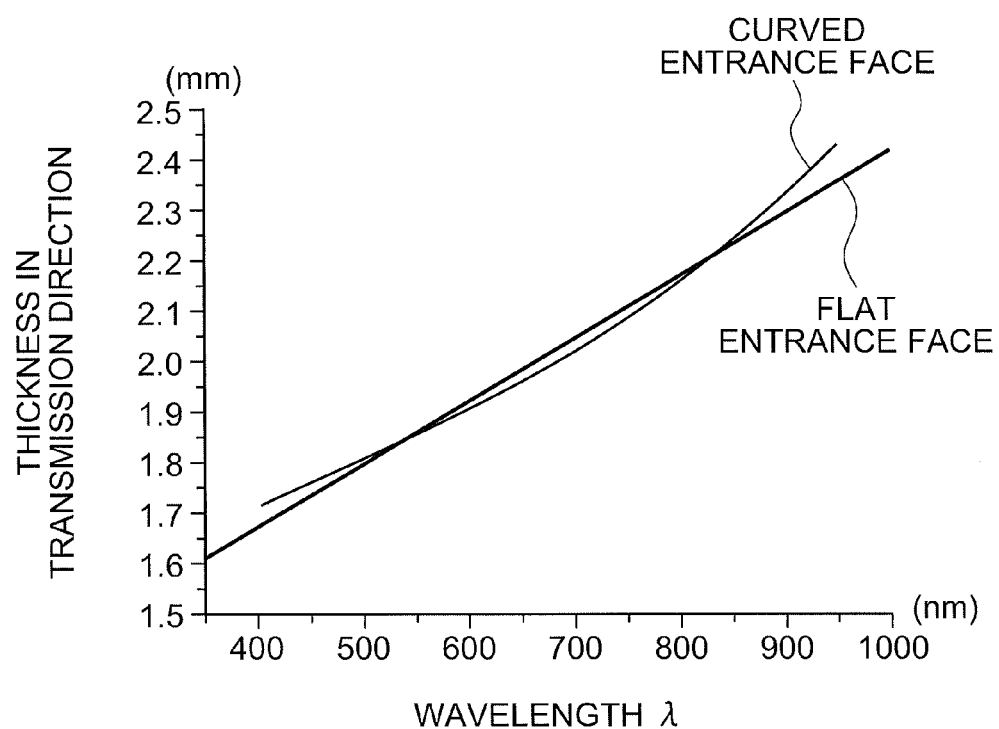
FIG. 7 is a graph illustrating the relationship between a thickness in the transmission direction of a polarization optical element of an embodiment and a wavelength.

FIG. 4 is a diagram describing the separation of polarization components in typical optical element P formed with a fast axis inclined at θ=45 degrees. FIG. 5 is a graph illustrating the relationship between a beam separation interval and a wavelength. In addition, FIG. 6 is a configuration diagram illustrating the configuration of polarization optical element 250 of the present embodiment and FIG. 7 is a graph illustrating the relationship between a thickness in the transmission direction of polarization optical element 250 in the present embodiment and a wavelength.

In general, in an optical element having a birefringence characteristic, such as crystal, an incident light beam (hereinafter referred to as an "incident light beam" and in the present embodiment, an interference polarization beam entering polarization optical element 250) has a different refractive index for each of fast and slow axes. Accordingly, based on the relationship between the fast and slow axes and the optical axis of the incident light beam, each polarization component transmits through the optical element in a different direction.

For example, as shown in FIG. 4, in rectangular optical element P having a birefringence characteristic in which a fast axis and a slow axis are formed at right angles, when such fast axis has an inclination θ=45 degrees with respect to an entrance face, the incident light beams, which include a vertical polarization component and a horizontal polarization component, travel in different directions within such optical element P, as shown in FIG. 4, due to a phenomenon called "walk-off." Accordingly, at an exit face of such optical element P, the vertical polarization component and horizontal polarization component of the incident light beams exit in the same direction; however, they exit along different optical axes spaced apart with a predetermined distance (hereinafter also referred to as a "beam separation interval") therebetween.

Furthermore, in such optical element P, even the same polarization components differ in refractive index in each of the fast and slow axes, depending on the wavelength, and thus, light beams having the same polarization component but with different wavelengths transmit through such optical element P in different directions.

In general, in an optical element having a polarization characteristic, it is known that the refractive index changes for each wavelength, and thus, the refractive indices of the fast and slow axes also change in association with the change in wavelength. Accordingly, as shown in FIG. 5, the separation interval of the incident light beams separated, on a polarization component basis, due to the walk-off phenomenon, also differs depending on the wavelength. Therefore, in rectangular polarization optical element 250, as in FIG. 4, it is impossible to have the same separation distance between the different polarization components in the light beams, for all wavelengths, when the polarization components are output therefrom.

Accordingly, polarization optical element 250 of the present embodiment is configured such that, by forming such polarization optical element to fulfill certain conditions, which will be described below, in terms of the relationship between the fast and slow axes and the optical axis of the incident light beam (i.e. the interference polarization beam of each wavelength), polarization optical element 250 separates the incident light beam of each wavelength on a polarization component basis and allows for the respective separated polarization components of each wavelength to exit in the same direction in a spaced manner with a predetermined distance from each other, in all wavelengths.

In particular, polarization optical element 250 of the present embodiment has a configuration in which a transmission distance is varied on a wavelength basis, namely, a configuration in which a thickness in the transmission direction is varied on a wavelength basis. Accordingly, polarization optical element 250 is configured such that, when the polarization components of each wavelength exit from such polarization optical element 250, polarization optical element 250 maintains the separation distance from one polarization component to another polarization component in the identical wavelength so that it is the same (including substantially the same) for all wavelengths. Therefore, polarization optical element 250 allows for the separated polarization components to exit in the same direction but along different optical axes.

Namely, polarization optical element 250 of the present embodiment adjusts, on a wavelength basis, the outgoing direction of the polarization components exiting from the exit face of such polarization optical element 250 by adjusting the thickness in the transmission direction of the incident light beam (interference polarization beams separated on a wavelength basis). Therefore, polarization optical element 250 allows for, while maintaining the separation distance from one polarization component to another polarization component in the identical wavelength to be the same (including substantially the same) for all wavelengths when the polarization components exit, the separated polarization components to exit in the same direction but along different optical axes.

In particular, polarization optical element 250 of the present embodiment has, as predetermined conditions, a fast axis (an optical axis of a first refractive index) and a slow axis (an optical axis of a second refractive index), which are at right angles to each other, and is formed such that an angle θ between the optical axis of the interference polarization beam and the slow axis is 45 degrees (θ=45 degrees).

It should be noted that, in polarization optical element 250 of the present embodiment, the fast and slow axes are not limited to being at right angles, and it is sufficient when an angle α between the fast and slow axes is in the range of "0 degrees<α<180 degrees." In addition, the fast axis and the optical axis of the interference polarization beam are not limited to being at 45 degrees, and it is sufficient when the fast axis is non-parallel with the optical axis of the interference polarization beam when it enters polarization optical element 250.

Further, polarization optical element 250 is formed such that the thickness in the transmission direction, through which the interference polarization beam for each wavelength transmits, gradually increases from a first lateral face side to a second lateral face side and also such that such thickness differs for each wavelength. Polarization optical element 250 of the present embodiment is adapted such that an interference polarization beam with the shortest wavelength enters the entrance face of the first lateral face side, interference polarization beams with wavelengths which are longer gradually from the first lateral face side to the second lateral face side enters the entrance face between the first lateral face side and the second lateral face side, and an interference polarization beam with the longest wavelength enters the entrance face of the second lateral face side.

In particular, as shown in FIG. 6, polarization optical element 250 of the present embodiment is formed as a hexagonal optical element having: entrance face 251 with respect to which an interference polarization beam of each wavelength enters; top face 252 and bottom face 253 which are perpendicular to entrance face 251 and which each has a wedge shape (a wedge shape in a planar view); two lateral faces which are parallel with an optical axis of the interference polarization beam and which include first lateral face 254 including a short end of the wedge shape and second lateral face 255 including a long end of the wedge shape; exit face 256 which is arranged opposite to entrance face 251 and which is also arranged opposite to a face formed with sensor arrays 261, 262.

In particular, polarization optical element 250 of the present embodiment is formed such that the fast axis is inclined at an angle θ. Namely, polarization optical element 250 has the fast axis that is inclined at angle θ=45 degrees with respect to exit face 256. When the separation distance of polarization components to be separated (i.e. the distance interval of the sensor arrays) is denoted by "d", the refractive indices (first refractive indices) in the fast axis are denoted by "$n_{max1}$" and "$n_{min1}$", and the refractive indices (second refractive indices) in the slow axis are denoted by "$n_{max2}$" and "$n_{min2}$", polarization optical element 250 has a thickness "$L_{min}$" in the transmission direction at the minimum wavelength (first lateral face side thickness) and a thickness "$L_{max}$" in the transmission direction at the maximum wavelength (second lateral face side thickness), respectively indicated by Formulae 2 and 3.

$$Lmax = \frac{d}{\frac{[(n_{max1})^2 - (n_{max2})^2]\cdot\tan\theta}{(n_{max1})^2 + (n_{max2})^2\cdot(\tan\theta)^2}} \quad \text{[Formula 2]}$$

$$Lmin = \frac{d}{\frac{[(n_{min1})^2 - (n_{min2})^2]\cdot\tan\theta}{(n_{min1})^2 + (n_{min2})^2\cdot(\tan\theta)^2}} \quad \text{[Formula 3]}$$

Formulae 2 and 3 are formulae indicating, respectively, the relationship between the separation distance by which each polarization component is separated from another in the "walk-off" phenomenon, the respective refractive indices of the fast and slow axes, and the transmission distance (the thickness in the transmission direction) in the polarization optical element having a birefringence characteristic.

For example, when polarization optical element 250 of the present embodiment is composed of SiO, the fast axis is formed with an inclination of angle θ=45 degrees, distance interval "d" of the sensor arrays is 10 μm, refractive index $n_{min1}$ of the fast axis and refractive index $n_{min2}$ of the slow axis at the minimum (blue) wavelength of 450 nm are 1.539441 and 1.54687209, respectively, and refractive index $n_{max1}$ of the fast axis and refractive index $n_{max2}$ the slow axis at the maximum (red) wavelength of 900 nm are 1.53685918 and 1.54323161, respectively, a first lateral face side thickness $L_{min}$≈1.65 mm and a second lateral face side thickness $L_{max}$=2.3 mm are obtained.

In addition, according to the present embodiment, by adjusting the respective refractive indices based on distance interval "d" of the sensor arrays, angle θ of the fast axis and the material of polarization optical element 250, lengths "L" of the first lateral face and second lateral face of polarization optical element 250 may be defined. Accordingly, the polarization optical element can still be formed even without specifying the material, etc., and when shapes such as the lengths of the first lateral face and second lateral face are altered, various sensor arrays may also be used.

Furthermore, when thickness "L" of polarization optical element 250 at each wavelength is calculated based on Formulae 2 and 3 above, it is essentially sufficient when polarization optical element 250 has an entrance face formed by a curved surface so as to have the thickness indicated in FIG. 7 at each wavelength.

On the other hand, in the present embodiment, in order to facilitate fabrication of polarization optical element 250, the entrance face of such polarization optical element 250 is formed by a flat surface of a rectangle, etc. Namely, the entrance face of such polarization optical element 250 is formed in a linear manner from the first lateral face toward the second lateral face.

Namely, as shown in FIG. 7, when lengths "L" of the first lateral face and second lateral face are adopted appropriately, even when the entrance face is formed by a flat surface, the separation intervals in all wavelengths can still be made substantially the same.

As described above, optical tomographic imaging system 100 of the present embodiment allows for a reduction in the number of components, such as a retaining member for retaining detection device 260, as compared to the case in which a polarization beam splitter that causes the respective polarization components to exit along optical axes which are at right angles to each other and that requires two line sensors to be separately arranged at different locations, is used as polarization optical element 250. Therefore, it is possible to achieve miniaturization thereof and price reduction associated with such miniaturization.

In addition, optical tomographic imaging system 100 of the present embodiment has a configuration in which: the angle "α" formed by an acute angle between the fast axis and the slow axis is in the range of "0 degrees<α<180 degrees" (e.g. at a right angle, 90 degrees); each of the fast and slow axes is non-parallel (e.g. at 45 degrees) with the optical axis of the interference polarization beam when it enters polarization optical element 250; the thickness in the transmission direction in polarization optical element 250 gradually increases from the side on which an interference polarization beam with a short wavelength is incident toward the side on which an interference polarization beam with a long wavelength is incident.

Accordingly, optical tomographic imaging system 100 of the present embodiment allows for an easy and precise adjustment of the separation intervals when separating the polarization components on a wavelength basis in polarization optical element 250, and thus, each polarization component can be detected in an accurate manner.

In addition, in optical tomographic imaging system 100 of the present embodiment, the entrance face of polarization optical element 250 for the interference polarization beam is a flat surface, and thus, such polarization optical element 250 can easily be manufactured and, in turn, it is possible to achieve price reduction.

DESCRIPTION OF THE REFERENCE NUMERALS

100 Optical tomographic imaging system
110 Polarization beam generation unit
120 Optical splitter/coupler
130 Reference light unit
140 Inspection unit
150 Image generation unit
200 Detection unit
210 Polarization controller
220 Transformation lens
230 Diffraction grating
240 Transformation lens
250 Polarization optical element
260 Detection device
261 First line sensor
262 Second line sensor

The invention claimed is:

1. An ellipsometry system for analyzing an object to be measured using polarization, comprising:
   a polarization beam generation unit that has a light source, and generates a polarization beam based on an outgoing light beam emitted from the light source;
   a polarization beam splitter that splits the generated polarization beam into a first polarization beam and a second polarization beam;
   a reference polarization beam unit that generates, from the first polarization beam, a reference polarization beam to be used as reference light when generating a tomographic image;
   a measurement unit that irradiates the object to be measured with the second polarization beam, and outputs an object-reflected polarization beam reflected from the object to be measured based on such irradiation;
   a detection unit that receives an interference polarization beam obtained by causing the reference polarization beam and the object-reflected polarization beam to interfere with each other and detects the interference polarization beam on a different polarization component basis; and
   a generation unit that generates the tomographic image of the object to be measured based on the polarization beam detected on a polarization component basis,
   wherein the detection unit has:
      a diffraction grating that separates the received interference polarization beam into a plurality of interference polarization beams on a wavelength basis as separated interference polarization beams;
      a polarization optical element that: has a birefringence characteristic including a first refractive index and a second refractive index; receives the separated interference polarization beams of the respective wavelengths in a wavelength order and in a parallel manner; separates the separated interference polarization beam of each wavelength into a plurality of separated interference polarization components on a polarization component basis as separated polarization components while transmitting the same, and outputs the respective separated polarization components in each wavelength in the same direction but along different optical axes; and
      a detection section that has two sensor arrays detecting light intensities of the interference polarization beams of each wavelength separated on a polarization component basis, respectively, the two sensor arrays being arranged side by side with a predetermined distance interval therebetween, and
   wherein the polarization optical element:
      has an entrance face slanted with respect to the traveling direction of the separated interference polarization beams when the separated interference polarization beams enter the polarization optical element:
      has a configuration in which each of separation distances is the same for all wavelengths, the separation distance being the distance from one separated interference polarization component to another separated interference polarization component in the identical wavelength; and
      is integrally and seamlessly formed, and
   wherein a thickness in a transmission direction in the polarization optical element through which the interference polarization beams transmit is different for each wavelength of the interference polarization beam, and gradually increases from a first lateral face side to a second lateral face side, the separated interference polarization beams with the shortest wavelength entering the entrance face of the first lateral face side, the separated interference polarization beams with wavelengths which are longer gradually from the first lateral face side to the second lateral face side entering the entrance face between the first lateral face side and the second lateral face side, the separated interference polarization beam with the longest wavelength entering the entrance face of the second lateral face side.

2. The ellipsometry system according to claim 1, wherein the thickness of the polarization optical element in the transmission direction gradually increases from a side on which an interference polarization beam having a short wavelength is incident to a side on which an interference polarization beam having a long wavelength is incident.

3. The ellipsometry system according to claim 2, wherein an entrance face of the polarization optical element for the interference polarization beams has a curved surface.

4. The ellipsometry system according to claim 2, wherein an entrance face of the polarization optical element for the interference polarization beams has a flat surface.

5. The ellipsometry system according to claim 1, wherein the relationship among the distance interval d of the two sensor arrays in the detection section, the first refractive index n1, the second refractive index n2, an angle q between an optical axis of the separated interference polarization beams and an axis of the first refractive index, and the thickness L in the transmission direction corresponding to at least one of a minimum wavelength and a maximum wavelength, satisfies Formula A:

$$L = \frac{d}{\frac{[(n_1)^2 - (n_2)^2] \cdot \tan\theta}{(n_1)^2 + (n_2)^2 \cdot (\tan\theta)^2}}.$$ [Formula A]

6. A detection unit to be used in an ellipsometry system for analyzing an object to be measured using polarization, the detection unit detecting, on a different polarization component basis, an interference polarization beam obtained by causing a reference polarization beam, which is used as reference light when generating a tomographic image and which is generated based on a predetermined polarization beam, and an object-reflected polarization beam, which is reflected from the object to be measured based on an irradiation of the object to be measured with the predetermined polarization beam, to interfere with each other, comprising:

a diffraction grating that separates the received interference polarization beam into a plurality of interference polarization beams on a wavelength basis as separated interference polarization beams;

a polarization optical element that: has a birefringence characteristic including a first refractive index and a second refractive index; receives the separated interference polarization beams of the respective wavelengths in a wavelength order and in a parallel manner; separates the separated interference polarization beam of each wavelength into a plurality of separated interference polarization components on a polarization component basis as separated polarization components while transmitting the same, and outputs the respective separated polarization components in each wavelength in the same direction but along different optical axes; and a detection section that has two sensor arrays detecting light intensities of the interference polarization beams of each wavelength separated on a polarization component basis, respectively, the two sensor arrays being arranged side by side with a predetermined distance interval therebetween, and wherein the polarization optical element:

has an entrance face slanted with respect to the traveling direction of the separated interference polarization beams when the separated interference polarization beams enter the polarization optical element:

has a configuration in which each of separation distances is the same for all wavelengths, the separation distance being the distance from one separated interference polarization component to another separated interference polarization component in the identical wavelength; and is integrally and seamlessly formed, and wherein a thickness in a transmission direction in the polarization optical element through which the interference polarization beams transmit is different for each wavelength of the interference polarization beam, and gradually increases from a first lateral face side to a second lateral face side the separated interference solarization beams with the shortest wavelength entering the entrance face of the first lateral face side, the separated interference polarization beams with wavelengths which are longer gradually from the first lateral face side to the second lateral face side entering the entrance face between the first lateral face side and the second lateral face side, the separated interference polarization beam with the longest wavelength entering the entrance face of the second lateral face side.

* * * * *